United States Patent [19]

Santaniello et al.

[11] Patent Number: 5,498,633
[45] Date of Patent: Mar. 12, 1996

[54] ESTERS OF ACYL CARNITINES WITH LONG-CHAIN ALIPHATIC ALCOHOLS AND PHARMACEUTICAL COMPOSITIONS CONTAINING SAME HAVING ANTIBACTERIAL ACTIVITY

[75] Inventors: Mosè Santaniello, Casoria; Maria O. Tinti; Domenico Misiti, both of Rome; Piero Foresta, Pomezia, all of Italy

[73] Assignee: Sigma-Tau Industrie Farmaceutiche Riunite S.p.A., Rome, Italy

[21] Appl. No.: 408,394

[22] Filed: Mar. 22, 1995

Related U.S. Application Data

[62] Division of Ser. No. 250,107, May 26, 1994, which is a continuation of Ser. No. 710, Jan. 5, 1993, abandoned.

[30] Foreign Application Priority Data

Jan. 16, 1992 [IT] Italy .................. RM92A0027

[51] Int. Cl.⁶ .................................................. A61K 31/225
[52] U.S. Cl. ................................................................ 514/547
[58] Field of Search .............................. 514/547; 560/170

[56] References Cited

U.S. PATENT DOCUMENTS

| | | | |
|---|---|---|---|
| 4,018,821 | 4/1977 | Tenud | 560/170 |
| 4,021,480 | 5/1977 | Tenud | 560/170 |
| 4,439,438 | 3/1984 | Cavazza | 560/170 |
| 4,443,475 | 4/1984 | Cavazza | 560/170 |
| 4,551,477 | 11/1985 | Cavazza | 560/170 |

FOREIGN PATENT DOCUMENTS 2096136  10/1982  United Kingdom .................. 560/170

*Primary Examiner*—Michael L. Shippen
*Attorney, Agent, or Firm*—Oblon, Spivak, McClelland, Maier & Neustadt

[57] ABSTRACT

Esters of acyl L-carnitines of general formula (I)

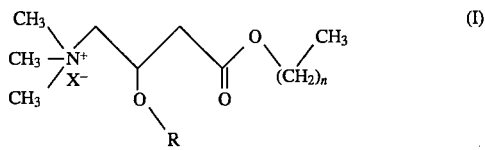

wherein R is a straight or branched acyl group having 2 to 16 carbon atoms, in particular isobutyryl and isovaleryl;

n is an integer comprised between 7 and 15, particularly 10; and,

X− is the anion of a pharmacologically acceptable acid are endowed with potent antibacterial activity. Pharmaceutical compositions comprising an ester of formula (I) can be utilized in human therapy and in the veterinary field.

11 Claims, No Drawings

ESTERS OF ACYL CARNITINES WITH LONG-CHAIN ALIPHATIC ALCOHOLS AND PHARMACEUTICAL COMPOSITIONS CONTAINING SAME HAVING ANTIBACTERIAL ACTIVITY

This is a division of application Ser. No. 08/250,107 filed on May 26, 1994, which is a Rule 62 continuation of application Ser. No. 08/000,710, filed Jan. 5, 1993, now abandoned.

The present invention relates to esters of acyl L-carnitines with long-chain aliphatic alcohols, of general formula (I)

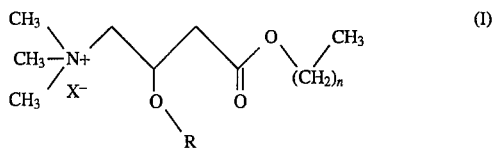

wherein R is a straight or branched acyl group having from 2 to 16, preferably from 4 to 12, carbon atoms, in particular isobutyryl and isovaleryl;

n is an integer comprised between 7 and 15, particularly 10, and

X− is the anion of a pharmacologically acceptable acid.

Among the esters of formula (I) Isovaleryl L-carnitine undecil ester and isobutyryl L-carnitine undecil ester are particularly preferred.

The esters of formula (I) are endowed with a potent antibacterial activity against Gram$^+$ and Gram$^-$ bacteria, In particular against bacteria of the genera Campylobacter and Helicobacter, which are respectively the aetlologic agents of intestinal infections in humans and of intestinal and genital infections in animals (*Campylobacter fetus, jejuni, coli*) or responsible of B-type gastrills and duodenal ulcer in humans (*Helicobacter pylori*).

Therefore, the present invention also relates to orally or parenterally administrable pharmaceutical compositions useful in human therapy for the treatment of intestinal infections, B-type gastritis and duodenal ulcer and also relates to pharmaceutical compositions useful for the treatment of intestinal and genital infections in animals.

The genus Campylobacter which encompasses microaerophilic Gram negative bacteria has recently drawn the attention of microbiologists because its role as aetiologic agent has been ascertained in a number of human and animal pathologies of growing Impact and increasingly difficult treatment.

Numerous strains appear to exhibit intrinsic resistance to many antibiotics, probably due to the inability of the drug (Bacitracin, Novobiocin, Rifampicin, Streptogramin B, Trimethoprim, Vancomycin, Cephalotyn) to penetrate the bacteria cells.

Other types of resistance may be correlated to acquired resistance of both plasmid type (Tetracycine, Kanamycin, Chloramphenicol) with subsequent ribosomial protection or 3'-aminoglycostde phosphotransferase production, and chromosomial type (Streptomycin, Spectinomycin, Erythromycin, Ampicillin, Nalidixlic acid) brought about by the production of 6-amnioglycoside nucleotransferase or β-lattamase.

Recently, on the basis of recent advances in their culture, biochemistry, morphology and susceptibility to antibiotics, the genus Helicobacter comprising the species *pylori* and *mustelae* has been differentiated from the genus Campylobacter.

The species *fetus, jejuni* and *coli* of the genus Campylobacter were shown to be responsible for intestinal infections in humans and for intestinal and genital infections in animals.

On the other hand, the genus Helicobacter has been linked to B-type gastritis in humans, since it was repeatedly found in the inflammatory tissue of the gastric mucosa of patients with gastritis (Marshall B. J. WARREN J. R., 1984, Unidentified curved bacilli in the stomach of patients with gastritis and peptie ulceration, LANCET. 1:1311–1313).

A very close relationship has been recently hypothesized among the infection by *H. pylori*, type-B gastritis, duodenal ulcer and gastric carcinoma (BLASER M. J. 1990, "Helicobacter pylori" and the Pathogenests of Gastroduodenal Inflammation. The J. of Infect. Dis. 161: 626–633).

A strong interest for developing new compounds endowed with antibacterial activity against the genus Helicobacter and, subordinately, against the genus Campylobacter can be accounted for on the grounds of the foregoing studies and the high frequency of relapses noticed in the last years.

The esters of formula (I) may be prepared following two distinct synthesis processes. The first process (illustrated in the synthesis scheme 1) comprises the steps consisting of:

(a) halogenating an acyl L-carnitine with a halogenating agent, such as thionyl chloride and oxalyl chloride (molar ratio comprised between 1:1 and 1:4) in an anhydrous organic inert solvent such as acetonitrile or methylene chloride at a temperature comprised between 0° C. and 30° C. for 1–4 hours, concentrating the raw reaction product and using it in the following step;

(b) dissolving the acid chloride of step (a) in an anhydrous organic inert solvent such as acetonitrile or methylene chloride and adding the alcohol diluted in the same solvent at a ratio comprised between 1:1 and 1:2, at a temperatures comprised between 0° C. and 30° C. for 2–10 hours, concentrating the solution and, if needed, purifying the compound by chromatography on silica gel; and (c) eluting the product dissolved in water or in an organic solvent on a strongly basic ion exchange resin such as Amberlite IRA 402 or on a weakly basic ion exchange resin such as Amberlist A 21, activated with tile desired HX acid and isolating the end product by lyophilization or concentration.

The second process (illustrated in the synthesis scheme 2) comprise the steps consisting of:

(a') reacting carnitine or an acyl carnitine inner salt with the relevant alkyl halogcnide (preferably bromide or iodide) in an organic anhydrous inert solvent at a temperature comprised between 30° C. and 60° C. for 8–24 hours and then isolating the resulting compound by concentration;

(b') acylating the ester obtained in step (a') with the desired acid chloride by known techniques, in case the starting compound in step (a') is carnitine;

(c') eluting an aqueous or alcoholic solution of the compound of step (a') or (b') on an ion exchange resin, such as Amberlite IRA 402 or Amberlist A 21 activated with the desired HX acid.

The anion X$^-$ of the pharmacologically acceptable acid is preferably selected from chloride: bromide; iodide; aspartate, particularly acid asparatate: citrate, particularly acid citrate; tartrate; phosphate, particularly acid phosphate; fumarate, particularly acid fumarate; glycerophosphate; glucosephosphate: lactate; maleate. particularly acid maleate: orotate; oxalate, particularly acid oxalate: sulphate, particularly acid sulphate: trichloroacetate; trifluoroacetate and methansulphonate.

SYNTHESIS SCHEME 1

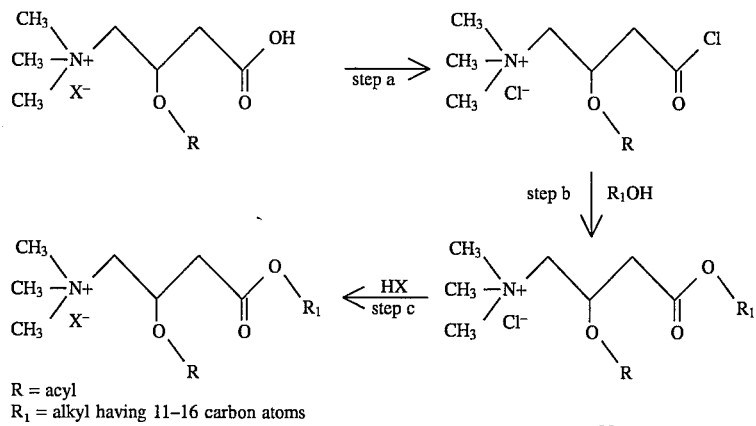

R = acyl
R₁ = alkyl having 11–16 carbon atoms

SINTHESIS SCHEME 2

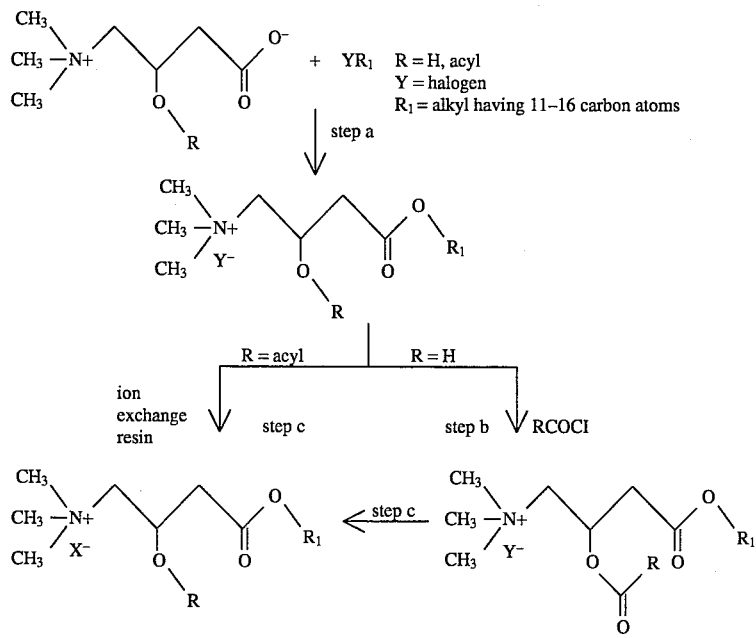

R = H, acyl
Y = halogen
R₁ = alkyl having 11–16 carbon atoms

EXAMPLE 1

Preparation of Isovaleryl-L-Carnitine Undecyl Ester Chloride (ST 722)

Step A: Preparation of Isovaleryl-L-carnitine chloride acid chloride.

Isovaleryl-L-carnitine chloride (30 g: 0.106 moles) was suspended in 100 ml anhydrous $CH_2Cl_2$.

The mixture was cooled at 0° C. and oxalyl chloride (13 ml; 0.15 moles) diluted in 15 ml anhydrous $CH_2Cl_2$ was slowly added under stirring.

After 30 minutes at room temperature, a further amount of oxalyl chloride (19 ml; 0.21 moles) diluted in 10 ml anhydrous $CH_2Cl_2$ was added.

The resulting solution was kept under stirring for 2 hours at room temperature, then concentrated under vacuum.

The residue thus obtained was washed twice with anhydrous $CH_2Cl_2$ and concentrated under vacuum.

The raw product thus obtained was used as such in the next reaction.

Step B: Preparation of Sovaleryl-L-carnitine undecyl ester chloride (ST 722).

The acid chloride previously prepared (0.106 moles) was dissolved in anhydrous $CH_2Cl_2$ (40 ml).

The solution was cooled at 0° C. and undecylic acid (35 ml; 0.168 moles) diluted in 35 ml $CH_2Cl_2$ was added in a nitrogen atmosphere.

The solution was kept under stirring at room temperature for 2 hours and then concentrated under vacuum until an oily residue was obtained.

The raw reaction mixture was chromatographed on a silica gel column buffered with 2% $Na_2HPO_4$, eluting with $CH_2Cl_2$ till complete elution of undecylic alcohol and then with $CH_2Cl_2$—MeOH 9:1 till complete elution of the compound.

The pooled fractions were concentrated and gave 28 g of the title compound; Yield 60%.
$[\alpha]_D^{25} = -10.5$ (c=1% $H_2O$))
Elementary analysis for $C_{23}H_{46}ClNO_4$

|  | C % | H % | Cl % | N % |
|---|---|---|---|---|
| Calculated (anhydrous) | 63.35 | 10.63 | 8.13 | 3.21 |
| Found | 60.87 | 0.88 | 8.14 | 3.29 |

$H_2O$ 2.4%
HPLC
Column: Spherisorb Cl 15 μm
t.: 50° C.
Eluant: $CH_3OH/KH_2PO_4$ 50 mM (65:35)
Flow rate: 1 ml/min.
Retention time: 14.82 min
NMR $CDCl_3$ δ5.5 (1H,m,—CH—); 4.2–3.8(4H,m,$N^+$ $CH_2$,$OCH_2$);
3.3(9H,S,$(CH_3)_3N^+$); 2.8(2H,m,$CH_2COO$); 2.2(2H,m,O-$COCH_2$);

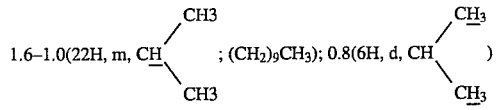

EXAMPLE 2

Preparation of Isobutyrly-L-Carnitine Undecyl Ester Chloride (ST 712)

The compound was prepared as described in example 1, substituting isobutyril L-earntine chloride, for isovaleryl L-earntine chloride. Yield 55%.
$[\alpha]_D^{25} = -15.8$ (C=1% $H_2O$)
Elementary analysis for $C_{22}H_{44}O_4NCl$

|  | C % | H % | Cl % | N% |
|---|---|---|---|---|
| Calculated (anhydrous) | 62.61 | 10.51 | 3.32 | 8.40 |
| Found | 61.77 | 10.67 | 3.29 | 8.17 |

$H_2O$ 0.8%
HPLC
Column: Spherisorb Cl (4.6 mm)
eluant $CH_3OH$—$KH_2PO_4$ 50 mM 60–40
Flow rate: 1 ml/min
Retention time: 14.75 min NMR $CDCl_3$ δ 5.5(1H, m, CH); 4.2–3.8(4H, m, $N^+CH_2$—; $OCH_2$); OCO

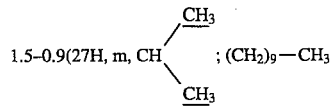

EXAMPLES 3–19

The compounds of Examples 3–19 were prepared following the procedures of the previous examples, as apparent to any average expert in organic synthesis. The physico-chemical characteristics of the compounds are summarized in the following table.

| Ex code | R | n | X⁻ | $[\alpha]_D^{25}$ | E.A. found C | H | N | Cl | H₂O | m.p. °C | HPLC Rt min | NMR δ |
|---|---|---|---|---|---|---|---|---|---|---|---|---|
| 3 ST 1000 | octanoyl | 10 | Cl⁻ | −10,7 (c = 1% CHCl₃) | C₂₆H₅₂NO₄Cl 62,84% | 10,7% | 3,03% | 6,96% | 3,2% | 103–105 | 10,28ᵃ | 5,7(1H, m, CHO); 4,3–4,0(4H, m, CH₂N⁺; OCH₂); 3,5(9H, s, (CH₃)₃N⁺); 2,8(2H, m, CH₂COO); 2,3(2H, t, OCOCH₂); 1,8(4H, m, 2 CH₂); 1,6(4H, m; 2 CH₂); 1,3(20H, broad, 10 CH₂); 0,9(6H, 2t, 2 CH₃),CDCl₃ |
| 4 ST 982 | undecanoyl | 10 | Cl⁻ | −14 (c = 0,5% MetOH) | C₂₉H₅₈NO₄Cl 66,65% | 11,72% | 2,70% | 6,93% | 0,4% | 133–135 | 16,32ᵇ | 5,6(1H, m, CHO); 4,1(2H, t, CCH₂); 3,9–3,7 (2H, m, CH₂N⁺); 3,3(9H, s, (CH₃)₃N⁺); 2,8 (2H, dd, CH₂COO); 2,4(2H, t, OCOCH₂); 1,6(4H, m, 2CH₂); 1,3 (30H, broad, 15CH₂); 0,9(6H, t, 2CH₃),CD₃OD |
| 5 ST 983 | palmitoyl | 10 | Cl⁻ | −14 (c = 1% MetOH) | C₃₄H₆₈NO₄Cl 69,42% | 11,84% | 2,36% | 5,96% | 0,8% | 158–159 | 10,5ᶜ | 5,6(1H, m, CHO); 4,1(2H, t, OCH₂); 3,9–3,7 (2H, m, CH₂N⁺); 3,2(9H, S, (CH₃)₃N⁺); 2,8(2H, m, CH₂COO); 2,4(2H, t, CCOCH₂); 1,6(4H, m, 2CH₂); 1,3(40H, broad, 20CH₂); 0,9(6H, t, 2CH₃),CD₃OD |
| 6 ST 1034 | isocaproyl | 10 | Cl⁻ | −13,12 (c = 0,8% H₂O) | C₂₄H₄₈NO₄Cl 61,28% | 11,10% | 3,12% | 9,01% | 1,9% | oil/not determined | 8,45ᵈ | 5,7(1H, m, CHO); 4,1(2H, t, OCH₂);4,0–3,7(2H, m, CH₂N⁺); 3,2(9H, s, (CH₃)₃N⁺); 3,0–2,7(2H, m, CH₂COO); 2,6–2,3(2H, m, OCOCH₂); 1,7–1,4(5H, m, 2CH₂,—CH); 1,3 (16H, broad, 8CH₂); 0,9(6H, d, (CH₃)₂); 0,8(3H, t, CH₃),D₂O |
| 7 ST 1036 | heptanoyl | 10 | Cl⁻ | −12,1 (c = 1% H₂O) | C₂₅H₄₉NO₄Cl 64,35% | 12,55% | 3,09% | 6,68% | 1,3% | not determined | 9,35ᵈ | 5,7(1H, m, CHO); 4,1(2H, t, CCH₂); 4,0–3,7 (2H, m, CH₂N⁺); 3,2(9H, s, (CH₃)₃N⁺); 3,0–2,7 (2H, m, CH₂COO); 2,5–2,3(2H, m, COCH₂); 1,6(4H, m, 2CH₂); 1,3(22H, m, 11CH₂); 0,9–0,8(6H, 2t, 2CH₃),D₂O |
| 8 ST 1050 | heptanoyl | 12 | Cl⁻ | −10,3 (c = 0,7% CHCl₃) | C₂₇H₅₄NO₄Cl 65,26% | 11,62% | 2,87% | 6,70% | 0,3% | dec. 150–160 | 9,13ᶜ | 5,7(1H, m, CHO); 4,3–4,0(4H, m, CH₂N⁺; OCH₂); 3,5(9H, s, (CH₃)₃N⁺); 2,8(2H, m, CH₂COO); 2,3(2H, m, OCOCH₂); 1,6(4H, m, 2CH₂); 1,3(26H, m, 13CH₂); 0,9(6H, 2t, 2CH₃),CDCl₃ |
| 9 ST 1051 | 2-methyl hexanoyl | 12 | Cl⁻ | −8,8 (c = 1% CHCl₃) | C₂₇H₅₄NO₄Cl 65,06% | 11,32% | 2,91% | 6,93% | 0,4% | not determined | 28,03ᵇ | 5,7(1H, m, CHO); 4,3–4,0(4H, m, CH₂N⁺; OCH₂); 3,5(9H, s, (CH₃)₃N⁺); 2,8(2H, m, CH₂COO); 2,4(1H, m, CH); 1,6(2H, m, |

| | | | | | | | | | | |
|---|---|---|---|---|---|---|---|---|---|---|
| 10 ST 1033 | isovaleryl | 12 | Cl⁻ | −11,8 (c = 1% H₂O) | C₂₅H₅₀NO₄Cl | 63,73% | 12,50% | 3,17% | 7,03% | 1,2% | dec. 150 | 9,39[d] | 5,7(1H, m, CHO); 4,1(2H, m, OCH₂); 4,0–3,7 (2H, m, CH₂N⁺); 3,2(9H, s, (CH₃)₃N⁺); 3,0–2,7(2H, m, CH₂COO); 2,3(2H, m, OCOCH₂); 2,1(1H, m, CH₂CH); 1,6(2H, m, CH₂); 1,3 (20H, broad, 11 CH₂); 0,9(6H, dd, CH(CH₃)₂); 0,8(3H, t, CH₃),D₂O CH₂); 1,3(26H, m, 13 CH₂); 1,1(3H, m, CHCH₃); 0,9(6H, 2t, 2CH₃),CDCl₃ |
| 11 ST 1052 | hexanoyl | 12 | Cl⁻ | −10,7 (c = 1% CHCl₃) | C₂₆H₅₂NO₄Cl | 65,01% | 11,87% | 2,93% | 7,14% | 1,2% | dec. 120–130 | 14,86[c] | 5,7(1H, m, CHO); 4,3–4,0(4H, m, CH₂N⁺; OCH₂); 3,5(9H, s, (CH₃)₃N⁺); 2,9–2,7(2H, m, CH₂COO); 2,3(2H, t, OCOCH₂); 1,6(4H, m, 2CH₂); 1,3(24H, broad, 12 CH₂); 0,9(6H, m, 2CH₃),CDCl₃ |
| 12 ST 1053 | octanoyl | 12 | Cl⁻ | −9,8 (c = 1% CHCl₃) | C₂₈H₅₆NO₄Cl | 66,46% | 11,93% | 2,71% | 6,93% | 0,7% | dec. 150–160 | 14,71[c] | 5,7(1H,m,CHO);4,3–4,0(4H,m, CH₂N⁺; OCH₂); 3,5(9H, s, (CH₃)₃N⁺); 2,9–2,7(2H, m, CH₂COO); 2,3(2H, m, CCOCH₂); 1,6(4H, m, 2CH₂); 1,3(28H, broad, 14 CH₂); 0,9(6H, m, 2CH₃),CDCl₃ |
| 13 ST 1037 | isovaleryl | 11 | Cl⁻ | −12,2 (c = 1% H₂O) | C₂₄H₄₈NO₄Cl | 63,46% | 12,26% | 3,15% | 7,81% | 1,0% | dec. 150–160 | 12,65[a] | 5,7(1H, m, CHO); 4,4–4,0(4H, m, N⁺CH₂; OCH₂) 3,5(9H, s, N⁺(CH₃)₃); 2,8(2H, m, CH₂COO); 2,2(2H, m, OCOCH₂); 2,0(1H,m,CH(CH₃)₂); 1,6 (2H,m,CH₂); 1,2(18H, broad, 9CH₂); 0,9–0,89H, d+t, CH₃; (CH₃)₂).CDCl₃ |
| 14 ST 1038 | isobutyryl | 11 | Cl⁻ | −14,5 (c = 1% H₂O) | C₂₃H₄₆NO₄Cl | 62,90% | 11,47% | 3,27% | 7,86% | 0,4% | dec. 150–155 | 14,0[a] | 5,7(1H, m, CHO); 4,4–4,0(4H, m, N⁺CH₂; OCH₂); 3,5(9H, s, N⁺(CH₃)₃); 2,9–2,7(2H, m, CH₂COO); 2,6–2,5(1H, m, CH(CH₃)₂); 1,6(2H, m, CH₂); 1,3(18H, broad, 9CH₂); 1,16H, d, CH(CH₃)₂); 0,8 (3H, t, CH₃).CDCl₃ |
| 15 ST 1060 | heptanoyl | 11 | Cl⁻ | −12,7 (c = 1% MetOH) | C₂₆H₅₂NO₄Cl | 67,00% | 12,12% | 2,41% | 6,60% | 0,6% | not determined | 10,47[f] | 5,7(1H, m, CHO); 4,4–4,0(4 H, m, N⁺CH₂; OCH₂); 3,5(9H, s, N⁺(CH₃)₃); 2,8(2H, m, CH₂COO); 2,4(2H, t, COOCH₂) 1,6(2H, m, CH₂); 1,3(26H, broad, 13 CH₂) |
| 16 ST 1001 | isovaleryl | 15 | Cl⁻ | −12,6 (c = 0,5% H₂O) | C₂₈H₅₆NO₄Cl | 65,30% | 11,11% | 2,68% | 7,57% | 0,5% | not determined | 12,12[a] | 5,7(1H, m, CHO); 4,4–4,0(4H, m, N⁺CH₂; OCH₂); 3,5(9H, s, N⁺(CH₃)₃); 2,8(2H, m, CH₂COO); 2,2(3H, m, CH(CH₃)₂); 1,6(2H, m, CH₂); 1,3(26H, |

-continued

| | | | | | | | | |
|---|---|---|---|---|---|---|---|---|
| 17 ST 1018 | isovaleryl | 10 | tartrate acid | −1,9 (c = 1% H$_2$O) | 56,87% 9,78% 2,44% C$_{27}$H$_{51}$NO$_{10}$ | 4% | not determined | 13,74[a] | broad, 13 CH$_2$); 1,0–0,9(9H, d+t, CH$_3$, CH(CH$_3$)$_2$).CDCl$_3$ 5,7(1H, m, CHO); 4,5(2H, s, 2CHOH); 4,1–3,6 (4H, m, N$^+$CH$_2$; OCH$_2$); 3,2(9H, s, N$^+$(CH$_3$)$_3$); 3,0–2,7(2H, m, CH$_2$COO); 2,4–2,2(2H, m, OCOCH$_2$); 2,1–2,0(1H, m, CH(CH$_3$)$_2$); 1,6(2H, m, CH$_2$); 1,3(16H, broad, 8CH$_2$); 0,9(6H, d, CH(CH$_3$)$_2$) 0,8(3H, t, CH$_3$).D$_2$O |
| 18 ST 1017 | isovaleryl | 10 | fumarate acid | −13,3% (c = 1% H$_2$O) | 62,23% 9,90% 2,54% C$_{27}$H$_{49}$NO$_8$ | 0,7% | dec. 120 | 13,99[a] | 6,6(2H, s, CH=CH); 5,7(1H, m, CHO); 4,1–3,7(4H, m, N$^+$CH$_2$;OCH$_2$); 3,2(9H, s, N$^+$(CH$_3$)$_3$); 3,0–2,7(2H, m, CH$_2$COO); 2,4–2,2 (2H, m, OCOCH$_2$); 2,0(1H, m, CH(CH$_3$)$_2$); 1,6(2H, m, CH$_2$); 1,3(16H, broad, 8CH$_2$); 0,9 (6H, d, CH(CH$_3$)$_2$); 0,8(3H, t, CH$_3$).D$_2$O |
| 19 ST 1032 | isovaleryl | 8 | Cl$^-$ | −17,4% (c = 1% H$_2$O) | 59,93% 10,25% 3,49% C$_{20}$H$_{40}$ClNO$_4$ | 8,84% | 1,7% | not determined | 5,75[b] | 5,7(1H, m, CHO); 3,8–4,1(4H, m, N$^+$CH$_2$; OCH$_2$); 3,3(9H, s, N$^+$(CH$_3$)$_3$); 2,8(2H, m, CH$_2$COO); 2,3(2H, m, COCH$_2$); 2,1(1H, m, CH(CH$_3$)$_2$); 1,6(2H, m, CH$_2$); 1,3(10H, m, broad); 1,0–0,9(9H, d+t, CH$_3$CH (CH$_3$)$_2$·D$_2$O |

[a]
Column: Nucleosil-SA(5μ)1,2 mm, i.d. 4,0 mm
T: 40 C.
mobile phase: (NH$_4$)$_2$HPO$_4$ 50 mM/CH$_3$CN 1:1 pH 4 con H$_3$PO$_4$
flow: 0,75 ml/min

[b]
Column: Spherisorb-Cl (5μ) 1,2 mm i.d. 4,6 mm
T: 50° C.
mobile phase: CH$_3$OH/KH$_2$PO$_4$ 50 mM 60:40
flow: 0,5 ml/min

[c]
Column: Spherisorb-Cl (5μ) 1,2 mm i.d. 4,6 mm
T: 50° C.
mobile phase: CH$_3$OH/KH$_2$PO$_4$ 50 mM 70:30 pH 3,9 con H$_3$PO$_4$
flow: 0,5 ml/min

[d]
Column: Spherisorb-Cl (5μ) 1,2 mm i.d. 4,6 mm
T: 40° C.
mobile phase: CH$_3$OH/KH$_2$PO$_4$ 50 mM 65:35 pH 4,5 con H$_3$PO$_4$
flow: 0,5 ml/min

[e]
Column: Nucleosil-SA(5μ) 1,2 mm i.d. 4,0 mm
T: 30° C.
mobile phase: (NH$_4$)$_2$HPO$_4$ 50 mM/CH$_3$CN 65:35 pH 3,5 con H$_3$PO$_4$
flow: 0,75 ml/min -continued f
Column: Spherisorb-Cl (5μ) 1,2 mm i.d. 4,6 mm
T: 40° C.
mobile phase: CH₃OH/KH₂PO₄ 50 mM 65:35 pH 4,5 con H₃PO₄
flow: 1 ml/min

ASSESSMENT OF BEHAVIOUR AND MORTALITY IN MICE

The assessment of normal behaviour in mice was carried out following S. Irwin's method (Psychopharmacologia, 13, 222 [1968]). This method allows alterations in some behavioural, neurophysiologic and neurovegetative parameters to be detected, which are directly observable by the researcher. The study was conducted using male Crl:(CD-1)(ICR)BR mice (Charles River-Italy) weighing 22–25 g, following oral administration of the compounds suspended in carboxymethylcellulose (0.5% by weight in $H_2O$) to groups of 4 animals/dose.

The animals were continuously kept under observation for five hours following treatment and twice a day in the subsequent five days. Mortality was also observed during the overall test period.

| Assessment of behaviour and mortality in mice. | | | |
|---|---|---|---|
| Compound | dose | Symptoms | Mortality |
| ST 712 | 1000 | NONE | 0/4 |
| ST 722 | 1000 | salivation, diarrhoea | 0/4 |

IMMUNOTOXICOLOGICAL STUDIES

Some Immunotoxicological results after oral ST 722 administration in mice are described hereinafter:

Test 1: Evaluation of the "In vitro-ex vivo" effect of repeated oral administrations of ST 722 on the primary antibody production (Jerne test) in the spleen of SRBC (Sheep Red Blood Cells) Immunized mice.

Experimental Procedure

Male $B_6D_2F_1$ mice (C. River) aged 8 weeks (6 animals each group) were utilized.

The substance (ST 722) was administered per os at the dose of 100 mg/kg/day from day −2 through day +2 (immunization at day 0). The animals were immunized by intraperitoneal route with a concentration of $1.0 \times 10^8$ cells/mouse in 0.2 ml of sterile saline. Five days later, spleens to be submitted to teasing process were removed from the animals sacrificed by cervical dislocation.

After standardization at $1.0 \times 10^7$ cells/ml, the splenocytes (0.1 ml) were mixed with warm agar-Hank's (2 ml) and 10% SRBC in PBS (0.2 ml) and seeded in Petri dishes (samples tested in triplicates) and incubated at 37° C. for 60 min.

After addition of complement (2 ml of guinea pig serum diluted 1:10 in Tris buffer), samples were further incubated at 37° C. for 30 min. To block the haemolysis reaction, the Petri dishes were cooled at 4° C. and the haemolysis plaques were counted.

The antibody response to SRBC is expressed as number of plaque forming cells (PFC) per $1.0 \times 106$ splenocytes as well as per spleen.

Results The results indicated that the repeated (5 consecutive days) oral administrations of ST 722 did not cause a statistically significant modification in PFC number after the antigenic challenge (Table 1). These data exclude the existence of an immunotoxic effect on the antibody-producer B lymphocytes.

The weight of the lymphold organs (spleen and thymus) did not show values relating to a toxic effect as-well (Tab. 1).

TABLE 1

Primary antibody production (Jerne test). Evaluation of the number of PFC (x ± S.E.) in the spleen of mice immunized with SRBC and treated per os with ST 722 at the dose of 100 mg/kg/day from day −2 through day +2 (immunization at day 0).

| Treatment | Body weight (g) | Spleen weight (mg) | Thymus weight (mg) | $PFC/10^6$ cells | PFC/ spleen |
|---|---|---|---|---|---|
| Control | 25.33 ± 0.38 | 95.50 ± 3.19 | 64.00 ± 1.51 | 202 ± 32 | 34228 ± 5064 |
| ST 722 | 25.12 ± 0.77 | 94.33 ± 4.12 | 59.50 ± 3.62 | 261 ± 34 | 44440 ± 6087 |

Test 2: Evaluation of the effect of repeated oral administrations of ST 722 on the weight of murine lymphoid organs (spleen and thymus).

Experimental procedure

Male $B_6D_2F_1$ mice (C. River) aged 7 weeks (7–8 animals each group) were orally treated with the substance ST 722 at the dose of 100 mg/kg/day for 7 consecutive days. Twenty-four hours after the last administration, the animals were sacrificed, the organs removed and weighed.

Results The performed treatment did not provoke any immunotoxic effect on the parameters examined (Table 2).

TABLE 2

Weight (x ± S.E.) of murine lymphoid organs after repeated treatment oral of the animals with the substance ST 722 (100 mg/kg/day for 7 consecutive days).

| Treatment | Body weight[a] (g) | Spleen weight[a] (mg) | Thymus weight[a] (mg) |
|---|---|---|---|
| Control | 24.00 ± 0.68 | 79.63 ± 3.31 | 51.88 ± 2.72 |
| ST 722 | 22.74 ± 0.37 | 77.88 ± 2.38 | 52.88 ± 3.20 |

[a]mean value (x ± E.S.) of 7–8 samples.

Test 3: Evaluation of the effect of repeated oral administrations of ST 722 on the body, spleen and thymus weight, and on the splenocyte concentration in mice.

Experimental procedure

Male $B_6D_2F_1$ mice (C. River) aged 10 weeks (5 animals each group) were orally treated with the substance ST 722 at the dose of 100 mg/kg/day for 5 consecutive days. Twenty-four hours after the last administration, the animals were sacrificed, the organs removed and weighed, and the splenocyte number determined.

Results The results, reported in Table 3, showed a lack of specific immunotoxic effects on the considered parameters following the scheduled ST 722 treatment.

TABLE 3

Weight of lymphoid organs and spleen concentration after repeated oral treatment of mice with the substance ST 722 (100 mg/kg/day for 5 consecutive days).

| Treatment | Body weight[a] (g) | Spleen weight[a] (mg) | Thymus weight[a] (mg) | Splenoc. number[b] ($\times 10^{-7}$) |
|---|---|---|---|---|
| Control | 27.70 ± 0.48 | 75.75 ± 2.36 | 41.75 ± 3.59 | 7.90 |
| ST 722  | 26.50 ± 0.53 | 73.25 ± 3.84 | 38.80 ± 3.01 | 7.85 |

[a] = mean value (x ± S.E.) of 5 samples.
[b] = value from 5 pooled samples.

Test 4: Evaluation of the effect of repeated oral administrations of ST 722 on the peritoneal macrophage number in mice.

Experimental Procedure

Male $B_6D_2F_1$ mice (C. River) aged 10 weeks (6 animals each group) were orally treated with the substance ST 722 at the dose of 100 mg/kg/day for 5 consecutive days. Twenty-four hours after the last administration, the animals were sacrificed, the peritoneal exudate cells (PEC) collected and the macrophage number determined.

Results

No toxic effect has been observed in PEC macrophage population; on the contrary, we measured an increase of about 60% in the peritoneal macrophages number of mice treated with the substance ST 722 (Table 4).

MICs were determined by a standard microdilution test, using serial two-fold dilutions of the substances in Mueller-Hinton broth.

The inoculum was prepared from an overnight culture in Mueller-Hinton broth matching the 0.5 Mc Farland (turbidity) standard (BRAY W.E., *Clinical Laboratory Methods*, 5th Ed. C. V. MOSBY, St. Louis, Mo., 1957), and was adjusted to a final concentration of $5.0 \times 10^4$ colony-forming units/ml.

Equal volumes (0.1 ml) of both bacterial suspensions and substance solutions were distributed in microtiter plates (Falcon, 96 wells, round bottom), and then placed in a humidified incubator (37° C.) for 18 hours.

TABLE 4

Peritoneal macrophage (Mø) number in mice treated with ST 722 (100 mg/kg/day for 5 consecutive days).

| Treatment | Body weight (g)[a] | PEC/mouse[b] ($\times 10^{-6}$) | PEC Mø[b] (%) | PEC Mø/Mouse[b] ($\times 10^{-6}$) |
|---|---|---|---|---|
| Control | 28.07 ± 0.63 | 2.14 | 53 | 1.13 |
| ST 722  | 28.13 ± 1.30 | 2.86 | 63 | 1.80 |

[a] = mean value ( ± S.E.) of 6 animals.
[b] = Value from 6 pooled samples.

MICROBIOLOGICAL STUDIES

Test 1: Evaluation of the Minimal Inhibitory Concentration (MIC) in broth of 15 new substances for Gram+ bacterial strains.

Experimental Procedure The following strains were used: *Staphylococcus aureus* (4); *Streptococcus faecalis* (8); *Bacillus pumilus* (1); *Bacillus subtilis* (1).

The tested substances were: ST 722, ST 982, ST 983, ST 1000, ST 1001, ST 1032, ST 1033, ST 1034, ST 1036, ST 1037, ST 1038, ST 1050, ST 1051, ST 1052, ST 1053.

The results, in terms of MIC values, resistant strain number and mean MIC values versus susceptible strains, are illustrated in Tables 1–6.

In order to establish the type of activity (-static or -cidal) exerted by the substances, the MBC (minimal bactericidal concentration) was determined by subculturing to agar 5 μl from each well where no visible growth had occurred.

Five strains and 10 substances were tested in this way (data not 5 shown), and the absolute coincidence of MIC and MBC values demonstrated that the substances have a bactericidal effect.

TABLE 1

Minimal Inhibitory Concentration (mcg/ml) of 5 Isovaleryl L-Carnitine esters for Graim+ bacterial strains.

| Bacterial strains | ST 1032 | ST 722 | ST 1037 | ST 1033 | ST 1001 |
|---|---|---|---|---|---|
| *Staphylococcus aureus* (303)        | 100  | 6.25 | 3.12 | 3.12 | 6.25 |
| *Staphylococcus aureus* (306 MR)     | n.d. | 6.25 | 3.12 | 3.12 | 6.25 |
| *Staphylococcus aureus* (ATCC 14154) | 50   | 3.12 | 3.12 | 3.12 | 6.25 |
| *Staphylococcus aureus* (LC1)        | 12.5 | 1.56 | 3.12 | 1.56 | 12.5 |
| *Streptococcus faecalis* (501)       | 50   | 3.12 | 3.12 | 3.12 | 3.12 |
| *Streptococcus faecalis* (505)       | 25   | 3.12 | 3.12 | 1.56 | 3.12 |
| *Streptococcus faecalis* (509)       | n.d. | 3.12 | 1.56 | 1.56 | 3.12 |

TABLE 1-continued

Minimal Inhibitory Concentration (mcg/ml) of 5 Isovaleryl L-Carnitine esters for Graim+ bacterial strains.

| Bacterial strains | ST 1032 | ST 722 | ST 1037 | ST 1033 | ST 1001 |
|---|---|---|---|---|---|
| *Streptococcus faecalis* (516) | n.d. | 1.56 | 1.56 | 1.56 | 3.12 |
| *Streptococcus faecalis* (518) | n.d. | 3.12 | 1.56 | 1.56 | 3.12 |
| *Streptococcus faecalis* (519) | n.d. | 3.12 | 1.56 | 1.56 | 3.12 |
| *Streptococcus faecalis* (R 2) | n.d. | 3.12 | 1.56 | 1.56 | 3.12 |
| *Streptococcus faecalis* (UM) | n.d. | 1.56 | 1.56 | 1.56 | 3.12 |
| *Bacillus pumilus* (CN 607) | n.d. | 1.56 | 1.56 | 1.56 | 6.25 |
| *Bacillus subtilis* (ATCC 6051) | n.d. | 3.12 | 3.12 | 3.12 | 12.5 |

TABLE 2

Mean MIC values (mcg/ml) of 5 Isovaleryl L-Carnitine esters for Gram+ bacterial strains.

| Compound | Mean MIC values* | Tested strains | Resistant strains (MIC >100) |
|---|---|---|---|
| ST 1032 | 47.50 | 5 | 0 |
| ST 722 | 3.12 | 14 | 0 |
| ST 1037 | 2.34 | 14 | 0 |
| ST 1033 | 2.11 | 14 | 0 |
| ST 1001 | 5.35 | 14 | 0 |

* = Mean MIC values versus susceptible strains.

TABLE 3

Minimal Inhibitory Concentration (mcg/ml) of 5 Undecyl L-Carnitine esters for Gram+ bacterial strains.

| Bacterial strains | ST 1034 | ST 1036 | ST 1000 | ST 982 | ST 983 |
|---|---|---|---|---|---|
| *Staphylococcus aureus* (303) | 3.12 | 3.12 | n.d. | >100 | >100 |
| *Staphylococcus aureus* (306 MR) | 3.12 | 3.12 | 3.12 | n.d. | n.d. |
| *Staphylococcus aureus* (ATCC 14154) | 3.12 | 3.12 | 1.56 | n.d. | n.d. |
| *Staphylococcus aureus* (LC 1) | 1.56 | 1.56 | 1.56 | 3.12 | >100 |
| *Streptococcus faecalis* (501) | 1.56 | 1.56 | n.d. | n.d. | n.d. |
| *Streptococcus faecalis* (505) | 1.56 | 1.56 | n.d. | n.d. | n.d. |
| *Streptococcus faecalis* (509) | 1.56 | 1.56 | n.d. | n.d. | n.d. |
| *Streptococcus faecalis* (516) | 1.56 | 3.12 | n.d. | n.d. | n.d. |
| *Streptococcus faecalis* (518) | 1.56 | 3.12 | 3.12 | 1.56 | >100 |
| *Streptococcus faecalis* (519) | 1.56 | 3.12 | 3.12 | 3.12 | >100 |
| *Streptococcus faecalis* (R 2) | 1.56 | 3.12 | n.d. | n.d. | n.d. |
| *Streptococcus faecalis* (UM) | 1.56 | 1.56 | n.d. | n.d. | n.d. |
| *Bacillus pumilus* (CN 607) | 1.56 | 1.56 | n.d. | n.d. | n.d. |
| *Bacillus subtilis* (ATCC 6051) | 3.12 | 3.12 | n.d. | n.d. | n.d. | n.d. = not determined.

TABLE 4

Mean MIC values (mcg/ml) of 5 Undecyl L-Carnitine esters for Gram+ bacterial strains.

| Compound | Mean MIC values* | Tested strains | Resistant strains (MIC >100) |
|---|---|---|---|
| ST 1034 | 2.00 | 14 | 0 |
| ST 1036 | 2.45 | 14 | 0 |
| ST 1000 | 2.49 | 5 | 0 |
| ST 982 | 2.60 | 4 | 1 |
| ST 983 | >100 | 4 | 4 |

* = Mean MIC values versus susceptible strains.

TABLE 5

Minimal Inhibitory Concentration (mcg/ml) of 5 L-Carnitine esters for Gram+ bacterial strains.

| Bacterial strains | ST 1038 | ST 1052 | ST 1051 | ST 1050 | ST 1053 |
|---|---|---|---|---|---|
| *Staphylococcus aureus* (303) | 6.25 | 3.12 | 6.25 | 6.25 | 6.25 |
| *Staphylococcus aureus* (306 MR) | n.d. | 3.12 | 12.5 | 6.25 | 6.25 |
| *Staphylococcus aureus* (ATCC 14154) | 3.12 | n.d. | n.d. | n.d. | n.d. |
| *Staphylococcus aureus* (LC 1) | 1.56 | n.d. | n.d. | n.d. | n.d. |
| *Streptococcus faecalis* (50 1) | 3.12 | 3.12 | 6.25 | 3.12 | 6.25 |
| *Streptococcus faecalis* (505) | 3.12 | n.d. | n.d. | n.d. | n.d. |
| *Streptococcus faecalis* (509) | 3.12 | 1.56 | 6.25 | 3.12 | 1.56 |
| *Streptococcus faecalis* (516) | 3.12 | n.d. | n.d. | n.d. | n.d. |
| *Streptococcus faecalis* (518) | 3.12 | n.d. | n.d. | n.d. | n.d. |
| *Streptococcus faecalis* (519) | 3.12 | n.d. | n.d. | n.d. | n.d. |
| *Streptococcus faecalis* (R 2) | 3.12 | n.d. | n.d. | n.d. | n.d. |
| *Streptococcus faecalis* (UM) | 3.12 | n.d. | n.d. | n.d. | n.d. |
| *Bacillus pumilus* (CN 607) | 3.12 | 1.56 | 1.56 | 1.56 | 1.56 |
| *Bacillus subtilis* (ATCC 6051) | 6.25 | n.d. | n.d. | n.d. | n.d. | n.d. = not determined.

TABLE 6

Mean MIC values (mcg/ml) of 5 L-Carnitine esters for Gram⁺ bacterial strains.

| Compound | Mean MIC values* | Tested strains | Resistant strains (MIC >100) |
|---|---|---|---|
| ST 1038 | 3.48 | 13 | 0 |
| ST 1052 | 2.49 | 5 | 0 |
| ST 1051 | 6.56 | 5 | 0 |
| ST 1050 | 4.06 | 5 | 0 |
| ST 1053 | 4.37 | 5 | 0 |

* = Mean MIC values versus susceptible strains.

Test 2: Evaluation of the Minimal Inhibitory Concentration (MIC) in broth of 16 new substances for Gram- bacterial strains.

Experimental Procedure

The following strains were used: *Enterobacter* (1), *Escherichia* (3), *Klebsiella* (3), *Proteus* (3); *Pseudomonas* (2); *Salmonella* (2), *Serratia* (1).

The tested substances were: ST 712, ST 722, ST 982, ST 983, ST 1000, ST 1001, ST 1032, ST 1033, ST 1034, ST 1036, ST 1037, ST 1038, ST 1050, ST 1051, ST 1052, ST 1053.

The results, obtained using the same procedure described in Test 1, are reported in Table 7–12.

TABLE 7

Minimal Inhibitory Concentration (mcg/ml) of 5 Isovaleryl L-Carnitine esters for Gram⁻ bacterial strains.

| Bacterial Strains | ST 1032 | ST 722 | ST 1037 | ST 1033 | ST 1001 |
|---|---|---|---|---|---|
| *Enterobacter aerogenes* (UM) | >100 | 25 | 25 | 100 | >100 |
| *Escherichia coli* (76 F) | n.d. | 25 | n.d. | n.d. | n.d. |
| *Escherichia coli* (92 F) | >100 | 25 | 100 | >100 | >100 |
| *Escherichia coli* (R 57B) | n.d. | 25 | n.d. | n.d. | n.d. |
| *Klebsiella aerogenes* (SH 1082) | n.d. | 25 | n.d. | n.d. | n.d. |
| *Klebsiella oxytoca* (552) | n.d. | 12.5 | n.d. | n.d. | n.d. |
| *Klebsiella pneumoniae* (7823) | n.d. | 12.5 | n.d. | n.d. | n.d. |
| *Proteus mirabilis* (32) | n.d. | >100 | n.d. | n.d. | n.d. |
| *Proteus morganii* (D.S.) | n.d. | 100 | n.d. | n.d. | n.d. |
| *Proteus vulgaris* (UM) | >100 | 50 | >100 | >100 | >100 |
| *Pseudomonas aeruginosa* (3 E) | >100 | 50 | >100 | >100 | >100 |
| *Pseudomonas aeruginosa* (10 E) | n.d. | 50 | n.d. | n.d. | n.d. |
| *Salmonella typhi* (J) | n.d. | 25 | n.d. | n.d. | n.d. |
| *Salmonella typhimurium* (D.S.) | >100 | 25 | >100 | >100 | >100 |
| *Serratia marcescens* (A/1) | n.d. | 50 | n.d. | n.d. | n.d. | n.d. = not determined.

TABLE 8

Mean MIC values (mcg/ml) of 5 Isovaleryl L-Carnitine esters for Gram⁻ bacterial strains.

| Compound | Mean MIC values* | Tested strains | Resistant strains (MIC >100) |
|---|---|---|---|
| ST 1032 | >100 | 5 | 5 |
| ST 722 | 35.67 | 15 | 1 |
| ST 1037 | 62.50 | 5 | 3 |
| ST 1033 | 100 | 5 | 4 |
| ST 1001 | >100 | 5 | 5 |

* = Mean MIC values versus susceptible strains.

TABLE 9

Minimal Inhibitory Concentration (mcg/ml) of 6 Undecyl L-CarrLitine esters for Gram⁻ bacterial strains.

| Bacterial Strains | ST 712 | ST 1034 | ST 1036 | ST 1000 | ST 982 | ST 983 |
|---|---|---|---|---|---|---|
| *Enterobacter aerogenes* (UM) | 25 | n.d. | n.d. | n.d. | n.d. | n.d. |
| *Escherichia coli* (76 F) | 25 | n.d. | n.d. | >100 | >100 | >100 |
| *Escherichia coli* (92 F) | 25 | 25 | 25 | n.d. | n.d. | n.d. |
| *Escherichia coli* (R 57B) | n.d. | 50 | >100 | n.d. | n.d. | n.d. |
| *Klebsiella aerogenes* (SH 1082) | n.d. | 25 | 100 | n.d. | n.d. | n.d. |
| *Klebsiella oxytoca* (552) | 12.5 | 12.5 | 50 | >100 | >100 | >100 |
| *Klebsiella pneumoniae* (7823) | 12.5 | 12.5 | 12.5 | n.d. | n.d. | n.d. |
| *Proteus mirabilis* (32) | >100 | >100 | >100 | n.d. | n.d. | n.d. |
| *Proteus morganii* (D.S.) | n.d. | 100 | >100 | n.d. | n.d. | n.d. |
| *Proteus vulgarts* (UM) | 100 | >100 | >100 | n.d. | n.d. | n.d. |
| *Pseudomonas aeruginosa* (3 E) | 50 | 50 | 100 | >100 | >100 | >100 |
| *Pseudomonas aeruginosa* (10 E) | 50 | 50 | >100 | n.d. | n.d. | n.d. |
| *Salmonella typhi* (J) | n.d. | 25 | 25 | n.d. | n.d. | n.d. |
| *Salmonella typhimurium* (D.S.) | 25 | 100 | >100 | >100 | >100 | >100 |
| *Serratia marcescens* (A/1) | 50 | n.d. | n.d. | n.d. | n.d. | n.d. | n.d. = not determined.

TABLE 10

Mean MIC values (mcg/ml) of 6 Undecyl L-Carnitine esters for Gram⁻ bacterial strains.

| Compound | Mean MIC values* | Tested strains | Resistant strains (MIC >100) |
|---|---|---|---|
| ST 712 | 36.38 | 15 | 1 |
| ST 1034 | 45.00 | 12 | 2 |
| ST 1036 | 60.71 | 12 | 5 |
| ST 1000 | >100 | 4 | 2 |
| ST 982 | >100 | 4 | 4 |
| ST 983 | >100 | 4 | 4 |

* = Mean MIC values versus susceptible strains.

TABLE 12

Mean MIC values (mcg/ml) of 5 L-Carnitine esters for Gram⁻ bacterial strains.

| Compound | Mean MIC values* | Tested strains | Resistant strains (MIC >100) |
|---|---|---|---|
| ST 1038 | 41.66 | 13 | 1 |
| ST 1052 | >100 | 5 | 5 |
| ST 1051 | >100 | 5 | 5 |
| ST 1050 | >100 | 5 | 5 |
| ST 1053 | >100 | 5 | 5 |

* = Mean MIC values versus susceptible strains.

TABLE 11

Minimal Inhibitory Concentration (mcg/ml) of 5 L-Carnitine esters for Gram⁻ bacterial strains.

| Bacterial Strains | ST 1038 | ST 1052 | ST 1051 | ST 1050 | ST 1053 |
|---|---|---|---|---|---|
| *Enterobacter aerogenes* (UM) | 25 | >100 | >100 | >100 | >100 |
| *Escherichia coli* (76 F) | n.d. | n.d. | n.d. | n.d. | n.d. |
| *Escherichia coli* (92 F) | 25 | >100 | >100 | >100 | >100 |
| *Escherichia coli* (R 57B) | 100 | n.d. | n.d. | n.d. | n.d. |
| *Klebsiella aerogenes* (SH 1082) | 50 | n.d. | n.d. | n.d. | n.d. |
| *Klebsiella oxytoca* (552) | 25 | >100 | >100 | >100 | >100 |
| *Klebsiella pneumoniae* (7823) | 25 | n.d. | n.d. | n.d. | n.d. |
| *Proteus mirabilis* (32) | >100 | n.d. | n.d. | n.d. | n.d. |
| *Proteus morganii* (D.S.) | 100 | n.d. | n.d. | n.d. | n.d. |
| *Proteus vulgarts* (UM) | 100 | >100 | >100 | >100 | >100 |
| *Pseudomonas aeruginosa* (3 E) | 100 | >100 | >100 | >100 | >100 |
| *Pseudomonas aeruginosa* (10 E) | 100 | n.d. | n.d. | n.d. | n.d. |
| *Salmonella typhi* (J) | 25 | n.d. | n.d. | n.d. | n.d. |
| *Salmonella typhimuriun* (D.S.) | 25 | n.d. | n.d. | n.d. | n.d. |
| *Serratia marcescens* (A/1) | n.d. | n.d. | n.d. | n.d. | n.d. | n.d. = not determined.

Evaluation of the Minimal Inhibitory Concentration (MIC) in agar of ST 722 and ST 712 for 3 Campytobacter and 1 Helicobacter strains.

In this experiment the activity of ST 722 and ST 712 against Campylobacter and Helicobacter was investigated. To better assess the "in vitro" activity of the compounds mentioned above against these bacteria, the agar dilution technique was chosen in that it is rather difficult ro readily sustain the growth of Campylobacter and notably Helicobacter in broth cultures.

Bacterial strains

The strains used were as follows:

*Campylobacter fetus* ATCC 27374. *Campylobacter coli* LI 048, *Campylobacter jejuni* 84-ISS, and *Helicobacter pytori* NCTC 11637.

The culture medium was Columbia agar base supplemented with 7% (V/V) defribinated horse blood (DHB) for Campylobacter strains, and the same medium additioned with Vitox (Oxoid) for Helicobacter strain.

The Campylobacter and Helicobacter strains, preserved at –80° C. in DHB containing 10% (V/V) glycerol, were thawed and grown, in their respective culture medium, in culture flasks, which were incubated for 48 hours at 37° C. in a 10% $CO_2$ atmosphere. After this first growth cycle, the bacteria were allowed to go through a second growth cycle in the same conditions as above.

The bacterial "patina" was then harvested by resuspension in 4–5 ml of Mueller-Hinton broth, the turbidity of which was then assessed according to Mc Farland's criteria (BRAY W.E., *Clinical Laboratory Methods*, 5th Ed. C. V. MOSBY, St. Louis, Mo., 1957).

The Helicobacter suspension was adjusted to an approximate concentration of $1.0 \times 10^9$ and $1.0 \times 10^8$ organisms/ml, while the Campylobacter suspension was adjusted to $1.0 \times 10^7$ and $1.0 \times 10^6$ organisms/ml.

With a Steers-type multipoint inoculator (STEERS E., FOLTZ E. L., GRAVES S., RIDEN J., 1959. *Inocula-replicating apparatus for routine testing of antibacterial susceptibility to antibiotics*. Antibiot, Chemoter. 9: 307–311) 1-µl volumes of the above standardized suspensions were spot-transferred into the wells of a 96-well microtiter plate, which had previously been filed with 0.2 ml/well of Mueller-Hinton agar 5% DHB, containing the test substances at different concentrations.

The plates was then incubated for 48/72 hours at 37° C. in a 10% $CO_2$ atmosphere.

Results

The MICs for Helicobacter and Campylobacter reported in Table 6 indicate that both ST 722 and ST 712 possess an antibacterial activity, the former compound being the most effective one.

Besides, the activity of the substances is not dependent upon the different infective inocula.

TABLE 6

MIC (mcg/ml) in agar of ST 722 and ST 712 for Campylobacter and Helicobacter strains.

| Bacterial strains | ST 722 | | ST 712 | |
|---|---|---|---|---|
| | I | II | I | II |
| *Helicobacter pylori* NCTC 11637 | 1.56 | 1.56 | 3.12 | 3.12 |
| *Campylobacter fetus* ATCC 27374 | 100. | 100 | 100 | 100 |
| *Campylobacter coli* LI 048 | 3.12 | 3.12 | 6.25 | 6.25 |
| *Campylobacter jejuni* 84-ISS | 12.5 | 12.5 | 25 | 50 |

I = inoculum of $1.0 \times 10^5$ cells/ml for Helicobacter and inoculum of $1.0 \times 10^3$ for Campylobacter.
II = inoculum of $1.0 \times 10^6$ cells/ml for Helicobacter and inoculum of $1.0 \times 10^4$ for Campylobacter.

Evaluation of the "in vitro" synergistic effect of ST 722 and Bismuth Subcitrate against a *Helicobacter pylori* strain.

Several studies have shown that Colloidal Bismuth Subcitrate (CBS) precipitates in the presence of the low pH of the gastric juice, and forms a complex with proteins on the ulcer base which may create a protective layer against agressive factors, thereby allowing healing of the ulcer lesion to occur (WAGSTAFF, A. J., BENFIELD, P. and MONK J. P., 1988. Colloidal Bismuth Subcitrate. A rewiew of its Pharmacodynamic and Pharmacoktnetic Properties, and its Therapeutic use in Peptic Ulcer Disease. Drugs 36, 132–157).

These observations together with the recent demonstration of an antibacterial activity of CBS versus Helicobacter (MIC values ranging from 4 to 32 mcg/ml) (Mc NULTY, C.A.M., DENT, j. and WISE, R., 1985. *Susceptibility of clinical isolates of "Campylobacter pyloridis"* to 11 antimicrobial agents. Antimicrob. Agents Chemoter. 28, 6, 837–838) have led several investigators to study the possible synergistic effect of CBS and antibiotics endowed with anti-Helicobacter activity aimed at obtaining a complete and persistent eradication of the bacteria from the stomach (VAN CAEKENBERGHE, D. L. and BREYSSENS, J., 1987. *In vitro synergistic activity between Bismute Subcitrate and various antimicrobial agents against Campylobacter pyloridis*" ("C. pylori"). Antimicrob. Agents Chemoter. 31, 9, 1429–1430).

In the light of these findings, we looked for a possible synergistic effect of CBS and ST 722 against a strain of *Helicobacter pylori*.

MATERIALS AND METHODS

Substances

CBS from the commercially available product De-Nol® (Gist-Brocades, Netherlad), i.e. ammonium and potassium double salt of colloidal bismuth citrate hydroxide, was utilized by preparing a suspension of 10 mg/ml CBS in 1N NaOH. After diluting 1:10 in Mueller-Hinton broth. 8 serial two-fold dilutions in the same medium were made. The compound ST 722 was dissolved In Mueller-Hinton broth at a starting concentration of 100 mcg/ml, then 7 serial two-fold dilutions were carried out.

Bacterial Strain

The "in vitro" anti-Helicobacter activity of both CBS and ST 722, alone and in association, was tested by utilizing the strain *H. pylori* NCTC 11637.

Inoculum Preparation

A 24-hour culture of Helicobacter in Columbia agar medium supplemented with Vitox (Oxoid) and 7% defribinated horse blood is washed with Mueller-Hinton broth.

Following densitometric evaluation (reading at 600 nm), the bacterial suspension was adjusted to a concentration of $1.0 \times 10^9$ cells/ml and 0.2-ml volumes were distributed into each well of a 96-well U-bottomed microtiter plate.

A 1-gl volume of this bacterial suspension was then distributed, by means of a Steers-type replicator apparatus, into the wells of microtiter plates containing the substances, either alone or In association. The final bacterial inoculum contained approximately $1.0 \times 10^6$ bacterial cells.

Experimental Procedure

The procedure described by Carrod et al. (GARROD, L. P. and WATERWORTH. P.M., 1962. *Methods of testing combined antibiotic bactericidal action and the significance of the results*J. Clin. Pathol. 15, 328–338) was utilized.

Briefly, 250-µl volumes of each test substance, either alone or admixed in all the possible combinations were additioned to 4.5 ml of Mueller-Hinton agar containing 5% defribinated serum. Volumes of 0.2 ml/well of the resulting solution were distributed into the wells of a microtiter plate, then seeded with 1 μl/well of a standardized bacterial suspension, and finally incubated for 48 hours at 37° C. in a 10% $CO_2$ atmosphere.

Criteria for the Evaluation of the Results

In order to evaluate the results obtained with combinations of antibiotics it was utilized the method (KROGSTAD, D. J. and MOELLERING, R. C.,1983. *Antimicrobial combinations*. In LORIAN, V., *Antibiotics in Laboratory Medicine*, 15, 537–549)based on the calculation of the Fractional Inhibitory Concentration Index (FIC index).

FIC index is calculated as follows:

$$FIC\ index = FIC_A + FIC_B = \frac{(A)}{(MIC_A)} + \frac{(B)}{(MIC_B)}$$

Where (A) is the MIC of substance A in the association and $(MIC_A)$ Is the MIC of the organism to substance A alone. $FIC_A$ is the fractional inhibitory concentration of substance A. (B), $(MIC_B)$ and $FIC_B$ are defined in the same fashion for substance B.

Based on these criteria, the effect of a combination of 2 substances is referred to as "synergistic" when the FIC index is <0.5, "additive" with a FIC index=1, and "antagonist" when FIC index is >1.

Finally, an "indifferent" effect occurs when the result with 2 substances is not significantly different from the result with the most effective substance alone, i.e. when FIC index= $FIC_A$ or $FIC_B$.

Results

The data reported in Table 6 show that the MIC of ST 722 and Bismuth Subcitrate against *H. pylori* is 1.56 mcg/ml and 6.25 mcg/ml, respectively.

The combination of the above substances results to be inhibitory at 0.19 mcg/ml ST 722 and 3.12 mcg/ml CBS.

The relevant FIC index is equal to 0.62, indicating that the association is not merely additive although not overly synergistic.

TABLE 6

Evaluation of the "in vitro" synergistic effect of ST 722 and Colloidal Bismuth Subcitrate (CBS) against *Helicobacter pylori*.

| Substances | MIC[a] | FIC[b] | FIC index[c] |
|---|---|---|---|
| ST 722 | 1.56 | 0.12 | |
| CBS | 6.25 | 0.50 | |
| ST 722 + CBS | 0.19 + 3.12 | | 0.62 |

[a] = minimal inhibitory concentration (mcg/ml).
[b] = fractional inhibitory concentration
[c] = fractional inhibitory concentration index.

Evaluation of the bactericidal effect of ST 722 against *Helicobacter pylori* (planktonic and sessile bacteria) and evaluation of the cytotoxic effect of ST 722 versus unifected or *H. pylori* infected HEp-2 cells.

The investigation aimed at evaluating the difference in susceptibility to ST 722 of planktonic and sessile Helicobacter cells, using in the latter case an "in vitro" experimental model, which closely resembled the clinical condition occurring "in vivo" in type-B gastritis. We used HEp-2 cells an epithelial cell line which harbors the same membrane glycolipid receptors for *H. pylori* as those harbored by the mucous cells of the antral gastric mucosa (MEGRAUD, F., TRIMOULET, P., LAMOULIATTE, H. and BOYANOVA. L.,1991. *Bacterial effect of Amoxicillin on "H. pylori" in an in vitro model using epithelial cells*. Antimicrob. Agents Chemoter. 35 (5): 869–872 and LINGWOOD, C. A., LAW, H. and PELLIZANI, A.,1989. *Gastric gtycerolipid as a receptor for Campylobacter pylori*. Lancet i: 238–241). Additionally, the viability of HEp-2 cells (either infected or not) was evaluated following "in vitro" ST 722 treatment. The degree of cytotoxicity was assessed by cytofluorimetric analysis of Propidium Iodine-stained HEp-2 cells.

MATERIALS AND METHODS

Cell Line

An HEp-2 epithelial cell line (a human larynx carcinoma) was used to permit the attachment of Helicobacter cells (sessile cells).

Bacterial Strain

*Helicobacter pylori* NCTC 11637.

HEp-2 Culture Medium

DMEM supplemented with 10% FCS.

Substance

The antibacterial and cytotoxic activity of ST 722 against Helicobacter and HEp-2 cells, respectively, was evaluated by using 3 different ST 722 concentrations, namely 0.1, 1.56 (i.e. the MIC value vs. *H. pylori* NCTC 116371 and 4 mcg/ml.

1. Experimental Procedure for the Evaluation of the Anti-Helicobacter Activity.

A confluent HEp-2 cell culture is prepared, which is obtained after incubating the cell line in tissue culture flasks for 24 hours (37° C., 10% $CO_2$, and ~96% humidity) in Columbia agar medium supplemented with Vitox and 7% defribinated horse serum. The bacteria are first harvested with DMEM medium 10% FCS, and then inoculated onto the HEp-2 cells to obtain a concentration of $5.0 \times 10^6$ CFU per flask (i.e. $2.0 \times 10^5$ $CFU/cm^2$).

Bacterial adhesion to the epitelial cells is favored by incubation for 2 hours at 37° C. and 5% $CO_2$. After washing to remove the non attached bacteria. ST 722 is added (5 ml of 3 different concentrations) to the HEp-2 cell culture flasks.

Two additional flasks are added with 5 ml medium lacking ST 722, as Helicobacter growth controls.

At a predetermined time, the flasks were taken, the medium was discarded, and the cells were washed. The cells were harvested with a rubber policeman in 1 ml of phosphate-buffered saline and disrupted with an Ultraturax homogenizer.

After making geometric dilutions of the suspensions (0.1 ml of each dilution inoculated onto each plate in triplicate), the plates were incubated for 7 days in a microaerobic atmosphere, and the plates with 30 to 200 CFU were counted.

The ST 722 activity against Helicobacter planktonic cells was determined in the same experimental conditions in the absence of HEp-2 cells. Finally, the results are expressed as CFU per flask of each sample with respect to the relevant control (i.e. sessile or planktonic cultures).

2. Experimental procedure for the evaluation of the HEp-2 cell viability.

The HEp-2 cells were seeded in 24-well plate at a concentration of $5.0 \times 10^4$ cells/well and incubated for 72 hours at 37° C. in a 5% $CO_2$ atmosphere to yield a confluent monolayer. After washing with Hank's (HBSS) solution, 1 ml of *H. pylori* suspension ($4.0 \times 10^5$ cells/ml) was added into each well.

After Incubating 2 hours at 37° C., to allow the bacteria to attach to the HEp-2 cell monolayer, the plates were washed once with HBSS, and ST 722 (at 3 different concentrations in DMEM 10% FCS) was finally added.

Three and twenty-four hours following ST 722 addition, the cells were transplanted and harvested by centrifugation at 800 g. The cell pellets were then resuspended in 500 μl PBS and additioned with 6 μl of a 1 mcg/ml Propidium Iodine stock solution in PBS. The same procedure was followed for the control, i.e. HEp-2 cells not infected with *H. pylori*. The cell suspensions were finally analyzed by means of a FAGScan cytofluorimeter.

Results

1. The Helicobacter strain utilized in this "in vitro" experimental model turned out to loosely attach to HEp-2 cells. In fact, starting from an inoculum of $1.0 \times 10^6$ cells only $9.5 \times 10^2$ cells did adhere to the epithelial cells after 3-hour incubation, increasing up to $4.2 \times 10^5$ following 24-hour incubation (Table 7). The number of sessile bacterial cells was reduced (approximately 50%) after a 3-h contact with 4 mcg/ml ST 722, while only 1.56 mcg/ml ST 722 was necessary to attain the same result after a 24-h contact. Similarly, ST 722 was more active against planktonic cells after incubation for 24 hours, being able to reduce the number of Helicobacter cells from $5.35 \times 10^8$ down to $1.85 \times 10^6$ at a concentration of 4 mcg/ml.

However, it has to be underlined that although ST 722 appeared to be more effective against planktonic cells, a complete medium sterilization was not attained.

It is likely that the adopted experimental conditions negatively interfered in obtaining the same result found in the experiment carried out in agar medium (MIC=1.56 meg/ml).

2. The selective staining of dead HEp-2 cells, detected by cytofluorimetric analysis of Propidium Iodine-stained cells, allowed to ascertain that ST 722 is devoid of any cytotoxicity versus HEp-2 cells.

The results indicate that even an ST 722 concentration of 4 mcg/ml, which was effective against Helicobacter sessile cells, was unable to induce detectable cytotoxicity versus the HEp-2 epithelial cells (data not shown).

TABLE 7

Bactericidal effect of ST 722 against *H. pylori* planktonic and sessile cells. The results are expressed as CFU per flask.

| Experimental samples | Sessile cells (CFU per flask) | Planktonic cells (CFU per flask) |
|---|---|---|
| 3-h contact | | |
| Control | $9.50 \times 10^2$ | $9.00 \times 10^5$ |
| 0.1 mcg/ml | $9.50 \times 10^2$ | $9.50 \times 10^5$ |
| 1.56 mcg/ml | $9.50 \times 10^2$ | $3.50 \times 10^5$ |
| 4.0 mcg/ml | $4.50 \times 10^2$ | $1.00 \times 10^5$ |
| 24-h contact | | |
| Control | $4.25 \times 10^5$ | $5.35 \times 10^8$ |
| 0.1 mcg/ml | $4.35 \times 10^5$ | $9.00 \times 10^7$ |
| 1.56 mcg/ml | $1.80 \times 10^5$ | $4.05 \times 10^6$ |
| 4.0 mcg/ml | $1.75 \times 10^5$ | $1.85 \times 10^6$ |

Evaluation of the protective effect of ST 722 in a subcutaneous experimental infection with *Staphylococcus aureus* in mice.

MATERIALS AND METHODS

Animals

Male $CD_1$ (C. River) mice aged 9 weeks were used (4 animals per group).

Bacterial Strain

A pathogenic strain of *Staphylococcus aureus* (*S. aureus* $Lc_1$), isolated from a systemic infection in nude mice, was utilized.

This strain possesses a virulence such that the $DL_{50}$ is equal to $7.3 \times 10^6$ cells/mouse, when i.p. inoculated in 5% gastric mucin. ST 722 exibited a MIC of 1.56 mcg/ml for the strain of *Staphylococcus* used.

Inoculum Preparation

The bacterial cells (kept under liquid nitrogen) are thawed and seeded in 10 ml of TSB medium and finally incubated for approximately 18 hours at 37° C.

The culture is then diluted in sterile saline so as to have $2.2 \times 10^7$ bacterial cells in a volume of 0.2 ml.

Treatment

Protocol 1

ST 722 was administered subcutaneously, immediately after bacterial inoculation, at the doses of 5, 20, and 50 mcg in 0.2 ml of sterile saline (single treatment).

Protocol 2

ST 722 was administered subcutaneously at a dose of 50 mcg (in 0.2 ml of sterile saline) immediately after bacterial Inoculation and again 5 hours later, 100 total meg per mouse (double treatment).

Experimental Procedure

The "in vivo" experimental model described by Grunberg et al. (GRUNBERG, E., BERGER. J., BESKID, G., CLEELAND, R., PRINCE, N. H. and TITSWORTH. E.,1967. Studies on the "in vitro" and "in vivo" chemotherapeutic properties of the antibiotics myxin. Chemotherapia 12, 272–281) was utilized.

Briefly, it consisted of a subcutaneous injection into the center of the abdominal wall of the standardized bacterial suspension followed by the s.c. administration of the substance in the same area according to the 2 protocols above.

After 24 hours, the animals were sacrificed, and the abdominal wall (including the peritoneum) was excised from each animal.

The tissue samples were first homogenized by a Potter-Elvehjem tissue grinder in 5 ml of a sterile saline, then a bacterial count was performed by plating the samples onto a *S. aureus* selective medium (Baird-Parker agar additioned with Eytellurite enrichment), which allows to easily detect the number of Staphylococcus colonies.

Evaluation of the Results

The number of colonies scored in a series of dilutions for each single sample consents to calculate the number of bacterial cells present in the infected tissue sample as follows:

$$\text{Number of bacteria} = \frac{\Sigma C_i}{\Sigma N_i Z_i}$$

Where $Z_i$ is the number of dilutions performed, $N_i$ is the number of plates prepared for each dilution, and $C_i$ is the total number of bacteria scored in each dilution.

Results

The subcutaneous infection induced in mice represents a particular model of topical infection, which is utilized to test the protective effect of a subcutaneous treatment with a substance, i.e. ST 722, whose penetration ability after simple local deposition on epidermis is not yet fully established.

Protocol 1

A dose of 5 mcg of ST 722 was unable to reduce the infective process, while doses of 20 e 50 mcg dose-dependently reduced in an appreciable manner the bacterial infection extent (Table 8), althought did not completely eradicate the bacteria from the tissue samples examined 24 hours following the bacterial inoculation.

Protocol 2

The same type of results were obtained after a double administration of ST 722 (50 mcg, twice). In this case, In fact, the treatment causes a reduction in the number of bacterial cells from $5.7 \times 10^7$ down to $3.1 \times 10^5$ (Table 13).

TABLE 8

Protective effect of ST 722 (single treatment) in a subcutaneous infective model with *S. aureus* in mice. Results are expressed as number of bacteria/mouse (mean values from 4 animals).

| Treatment | Number of bacteria/mouse |
|---|---|
| Control | $1.11 \times 10^8$ |
| ST 722 5 mcg | $1.21 \times 10^8$ |
| ST 722 20 mcg | $2.13 \times 10^6$ |
| ST 722 50 mcg | $5.61 \times 10^5$ |

TABLE 9

Protective effect of ST 722 (double treatment) in a subcutaneous infective model with *S. aureus* in mice. Results are expressed as number of bacteria/mouse (mean values from 4 animals).

| Treatment | Number of bacteria/Mouse |
|---|---|
| Control | $5.75 \times 10^7$ |
| ST 722 | $3.12 \times 10^5$ |

Evaluation of the antibacterial activity of the undecyl alcohol.

To ascertain whether the antimicrobial activity was due to the undecyl alcohol (a possible product from the hydrolysis of the undecyl esters, such as e.g. ST 722 and ST 712), different "in vitro" tests were performed to overcome the difficulties stemming from the insolubility of the undecyl alcohol in the assay medium.

To circumvent this problem, three different experimental approaches were chosen obtaining the following results:

1) Undecyl alcohol emulsified in Tween 80 and tested up to the concentration of 300 mcg/ml Jn agar seeded with 7 Gram-bacterial strains (Agar dilution test).

Results: no activity.

2) Undecyl alcohol absolute (0.05 ml) in agar seeded with 4 Gram-bacterial strains (Agar diffusion test).

Results: no activity.

3) Undecyl alcohol emulsified in Tween 80 and tested up to the concentration of 400 mcg/ml in broth seeded with 4 Gram-bacterial strains and 1 Gram⁺ bacterial strain (Broth dilution test).

Results: no activity.

We claim:

1. The process for treating a bacterial infection in a human or animal which comprises administering to the human or animal an antibacterially effective amount of an ester of acyl L-carnitine of the general formula

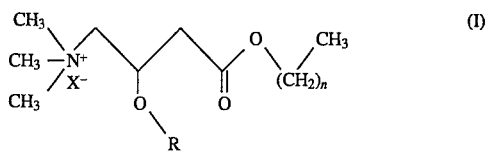

wherein:

R is a straight or branched saturated aliphatic hydrocarbon carboxylic acyl group having 2–16 carbon atoms, n is an integer from 7 to 15, and X⁻ is the anion of a pharmacologically acceptable acid.

2. The process of claim 1, wherein the bacterial infection is an infection by bacteria of the genus Campylobacter.

3. The process of claim 1, wherein the bacterial infection is an infection by bacteria of the genus Helicobacter.

4. The process for treating an intestinal infection in a human due to bacteria of the genus Campylobacter which comprises administering to the human an antibacterially effective amount of a compound of an ester of acyl L-carnitine of the general formula

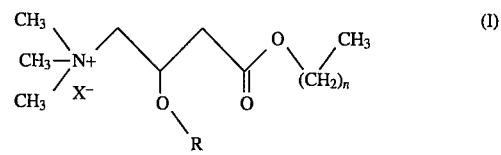

wherein:

R is a straight or branched saturated aliphatic hydrocarbon carboxylic acyl group having 2–16 carbon atoms, n is an integer from 7 to 15, and X⁻ is the anion of a pharmacologically acceptable acid.

5. The process for treating B-type gastrites or duodenal ulcer in a human due to a bacteria of the genus Helicobacter which comprises administering to the human an antibacterially effective amount of an ester of acyl L-carnitine of the general formula

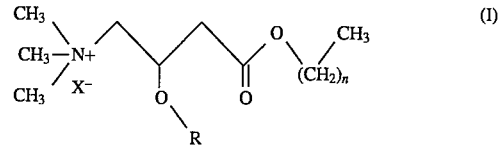

wherein:

R is a straight or branched saturated aliphatic hydrocarbon carboxylic acyl group having 2–16 carbon atoms, n is an integer from 7 to 15, and X⁻ is the anion of a pharmacologically acceptable acid.

6. The process for treating an intestinal or genital infections in an animal due to bacteria of the genus Campylobacter which comprises treating the animal with an antibacterially effective amount of an ester of acyl L-carnitine of the general formula

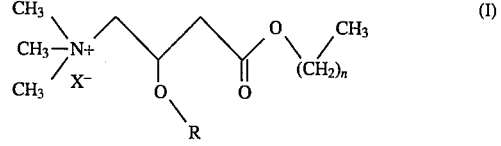

wherein:

R is a straight or branched saturated aliphatic hydrocarbon carboxylic acyl group having 2–16 carbon atoms, n is an integer from 7 to 15, and X$^-$ is the anion of a pharmacologically acceptable acid.

7. The process of claim 1 wherein R is isobutyryl or isovaleryl.

8. The process of claim 1 wherein n is 10.

9. The process of claim 1 wherein X$^-$ is selected from: chloride; bromide; iodide; acid asparatate; acid citrate; tartrate; acid phosphate; acid fumarate; glycerophosphate; glucosephosphate; lactate; acid maleate; orotate; acid oxalate; acid sulphate; trichloroacetate, trifluoroacetate and methansulphonate.

10. The process of claim 1 wherein the ester is isovaleryl L-carnitine undecyl ester chloride.

11. The process of claim 1 wherein the ester is isobutyryl L-carnitine undecyl ester chloride.

* * * * *